US006187058B1

(12) United States Patent
Massoni

(10) Patent No.: US 6,187,058 B1
(45) Date of Patent: *Feb. 13, 2001

(54) LOW WATER NO VOLATILE ORGANIC COMPOUND HAIR LIGHTENER AND DYEING COMPOSITION

(75) Inventor: Jack Massoni, Putnam Valley, NY (US)

(73) Assignee: Combe, Inc.,, White Plains, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/082,014

(22) Filed: May 20, 1998

(51) Int. Cl.$^7$ .................................................. A61K 7/13
(52) U.S. Cl. ...................................... 8/406; 8/405; 8/435
(58) Field of Search ............................... 8/405, 406, 435, 8/107, 111; 252/186.1; 510/367; 132/208; 424/62, 70.6

(56) References Cited

U.S. PATENT DOCUMENTS

| | | | |
|---|---|---|---|
| 3,634,013 | 1/1972 | Benshein et al. | 8/409 |
| 3,651,209 | 3/1972 | Cohen | 424/62 |
| 3,658,455 | 4/1972 | Kalopissis et al. | 8/409 |
| 3,677,690 | 7/1972 | Kalopissis et al. | 8/416 |
| 3,804,586 | 4/1974 | Kalopissis et al. | 8/415 |
| 3,811,830 | 5/1974 | DeMarco | 8/405 |
| 3,822,112 | 7/1974 | Zviak et al. | 8/405 |
| 3,951,589 | 4/1976 | Alperin et al. | 8/415 |
| 3,986,825 | 10/1976 | Sokol | 430/77 |
| 4,169,704 * | 10/1979 | Fakhouri | 8/421 |
| 4,171,952 * | 10/1979 | Fakhouri | 8/421 |
| 4,172,703 * | 10/1979 | Fakhouri | 8/412 |
| 4,195,972 | 4/1980 | Lapidus | 8/405 |
| 4,268,264 | 5/1981 | Grollier et al. | 8/410 |
| 4,295,848 | 10/1981 | Grollier et al. | 8/421 |
| 4,306,873 | 12/1981 | Lapidus | 8/405 |
| 4,310,329 * | 1/1982 | Holland | 8/405 |
| 4,314,810 | 2/1982 | Fourcadier et al. | 8/429 |
| 4,330,291 * | 5/1982 | Bugaut et al. | 8/408 |
| 4,331,443 * | 5/1982 | Kostka et al. | 8/671 |
| 4,337,061 * | 6/1982 | Bugaut et al. | 8/405 |
| 4,425,132 | 1/1984 | Grollier et al. | 8/405 |
| 4,556,876 * | 12/1985 | Brown et al. | 8/411 |
| 4,595,585 * | 6/1986 | Papantoniou et al. | 424/47 |
| 4,645,663 * | 2/1987 | Grollier et al. | 424/62 |
| 4,727,192 | 2/1988 | Junino et al. | 564/441 |
| 4,776,855 | 10/1988 | Pohl et al. | 8/406 |
| 4,838,894 * | 6/1989 | Kijek et al. | 8/412 |
| 4,923,478 * | 5/1990 | Naggiar | 8/161 |
| 4,927,627 | 5/1990 | Schrader et al. | 8/406 |
| 4,981,485 | 1/1991 | Motono | 8/405 |
| 5,026,401 | 6/1991 | Bugaut et al. | 8/408 |
| 5,104,414 * | 4/1992 | Tamura et al. | 8/408 |
| 5,281,240 | 1/1994 | McGee | 8/405 |
| 5,288,421 * | 2/1994 | Mandy | 8/142 |
| 5,376,146 | 12/1994 | Casperson et al. | 8/408 |
| 5,384,118 * | 1/1995 | LaValle | 424/70.13 |
| 5,391,400 | 2/1995 | Yang | 8/115.51 |
| 5,393,305 | 2/1995 | Cohen et al. | 8/406 |
| 5,496,401 | 3/1996 | Yang | 8/115.6 |
| 5,516,942 | 5/1996 | Lagrange et al. | 564/441 |
| 5,575,989 | 11/1996 | Caskey | 132/208 |
| 5,577,519 * | 11/1996 | Samain et al. | 132/208 |
| 5,622,691 | 4/1997 | Tricaud et al. | 424/62 |
| 5,651,793 | 7/1997 | Hoeffkes et al. | 8/406 |
| 5,656,280 | 8/1997 | Herb et al. | 424/401 |
| 5,693,101 * | 12/1997 | Audousset et al. | 8/408 |

FOREIGN PATENT DOCUMENTS

| | | |
|---|---|---|
| 0035364 | 9/1981 | (EP) . |
| 0223572 | 5/1987 | (EP) . |
| 2692573 | 12/1993 | (FR) . |
| 2129447 | 5/1984 | (GB) . |

\* cited by examiner

Primary Examiner—Caroline D. Liott

(57) ABSTRACT

A low or no VOC hair lightener or dying composition with a low water content and a high organic content comprising:
(a) a developer phase comprising:
  (i) water;
  (ii) an oxidizing agent; and
  (iii) optionally a thixotropic control agent; and
(b) a tint phase comprising:
  (i) 0–50 weight percent water;
  (ii) 0–10 weight percent dye;
  (iii) 10–50 weight percent of a non VOC solvent;
  (iv) 5–60 weight percent of a thickener;
  (v) a sufficient amount of an alkalizer so that the hair coloring composition has a pH of 6–12.

7 Claims, No Drawings

LOW WATER NO VOLATILE ORGANIC COMPOUND HAIR LIGHTENER AND DYEING COMPOSITION

BACKGROUND OF THE INVENTION

The present invention relates to a low or no volatile organic content (VOC) composition for dyeing hair and a process for dyeing hair. More specifically, the present invention relates to a hair dyeing composition with no VOC and a low water content.

It is well known to dye keratin fibers and in particular human hair with oxidative dyes such as diamines, aminophenols and/or phenols. These compounds are not generally dyes but are converted to dyes by condensation in an oxidizing medium.

The most prevalent manor of employing these oxidative dyes to dye human hair typically comprises a two component system. The two component system comprises a tint phase which contains the oxidation dye and a developer phase which contains a suitable oxidizing agent, such as hydrogen peroxide. The tint phase and the developer phase are mixed together and immediately applied to the hair. Upon application to the hair, the dyes penetrate into the hair and are oxidized to produce the desired hair color.

If an appropriate alkalizer is used in the tint phase, the combination of the alkalizer with the oxidizing agent in the developer phase may destroy some of the natural melanin pigment in the hair to produce hair with a lighter color or shade than the initial hair color.

These two part oxidative systems that contain a low viscosity tint phase and a low viscosity developer phase to allow for easy mixing and application have been commercially available for over thirty year under the trademarks, PREFERENCE BY L'OREAL, NICE N' EASY by Clairol, MISS CLAIROL CREME FORMULA by Clairol, COLORSILK by Revlon and COLOR CHARM by Wella. Examples of these prior art products are described in U.S. Pat. Nos. 5,376,146, 4,776,885 and 4,268,264 and are incorporated herein by reference.

Recent safety and environmental concerns by governmental agencies and private organizations have brought to light issues over the use of volatile organic compounds. In fact, many States have passed or are considering legislation that limits the VOC for various consumer products. Although no legislation has thus far impacted the VOC for hair coloring formulations, manufacturers are making a concerted effort to reduce if not eliminate volatile organic compounds, especially isopropanol and ethanol, from their hair coloring products.

The research into the reduction of the volatile organic compounds in hair coloring products has resulted in two types of products.

The first type of product uses a creme or gel that is supplied in a tube. The creme or gel is mixed with some type of dedicated developer that is commonly formulated with any of several types of non-ionic surfactants. These surfactants are required to allow ease of mixing and to produce a satisfactory consistency for stay-put ability when the mixture is applied to the hair.

The second method as described in U.S. Pat. No. 4,776,855 employs a high aqueous hair color vehicle that is combined with a developer containing a unique polymer that is stable to hydrogen peroxide. When the high aqueous tint phase is combined with the polymer containing-developer phase, the polymer swells to thicken the mixture and produce an oxidative hair dye mixture with satisfactory stay-put properties.

These two attempts at a reduced VOC hair coloring product have the disadvantages of requiring a specific dedicated developer that comprises materials needed to thicken the tint/developer mixture. These dedicated developers increase the cost of the product and complicate the manufacture of the product. These prior attempts at a reduced VOC hair coloring product also have the disadvantage of being limited to the dyes that can be used due in a high aqueous low organic content medium.

It is an object of the present invention to provide a hair coloring or dyeing composition with a reduced or no VOC that can be used for a wide variety of dyes and can be easily formulated.

It is a further object of the present invention to provide a tint phase for a hair coloring or dyeing composition with a reduced or no VOC that comprises less than fifty percent water.

It is also an object of the present invention to provide a hair coloring or dyeing composition with a reduced or no VOC that exhibits acceptable stay-put ability for the prescribed development time.

SUMMARY OF THE INVENTION

The foregoing objectives are met by a lightener or dyeing composition comprising:

(a) a developer phase comprising:
  (i) 63–99 weight percent, preferably 71–86 weight percent, of water;
  (ii) 1–30 weight percent, preferably 3–9 weight percent, of an oxidizing agent; and
  (iii) optionally 0–7 weight percent, preferably 3–5 weight percent, of a thixotropic control agent; wherein all the foregoing percentages are based upon the total weight of the developer phase alone, and (b) a tint phase comprising:
  (i) 0–50 weight percent, preferably 10–40 weight percent, of water;
  (ii) 0–10 weight percent, preferably 0.01–10 weight percent, of a dye;
  (iii) 10–50 weight percent, preferably 25–40 weight percent, of a non VOC solvent;
  (iv) 5–60 weight percent, preferably 10–50 weight percent, of a thickener; and
  (v) a sufficient amount of an alkalizer so that the hair coloring composition has a pH of 6–12, wherein all the foregoing percentages are based on the total weight of the tint phase alone.

By varying the amount of thixotropic agents and thickeners employed, the hair coloring or dyeing composition can be tailored for any specific need. For instance, lower amounts of thixotropic agents and thickeners can be used to obtain a composition with a viscosity of approximately 1,000 cps for shampoo-in products or higher amounts of thixotropic agents and thickeners can be used to obtain a composition with a viscosity of approximately 100,000 cps for professional bowl and brush applications.

The phrase "non VOC solvent" as used in this specification is a solvent that exhibits a vapor pressure of less than 0.1 mm Hg.

DETAILED DESCRIPTION OF THE INVENTION

The developer phase of the present invention in its most basic form comprises water and about 1 to about 30 weight percent of an oxidizing agent, preferably about 1 to about 15 weight percent and most preferably about 3 to about 9 weight percent based on the total weight of the developer phase. The oxidizing agent may be a compound such as urea peroxide, melamine peroxide, perborates, such as sodium perborate, percarbonates such as sodium percarbonate or mixtures of the foregoing. The most preferred oxidizing agent is hydrogen peroxide.

The developer phase may also contain thixotropic control agents such as the polymers described in U.S. Pat. Nos. 5,376,146 and 4,776,885, incorporated herein by reference, or stabilizers such as phenacetin or ethylene diamine tetracetic acid (EDTA).

The viscosity of the developer phase is from about 1 cps to about 5,000 cps by weight, preferably about 1 cps to about 500 cps by weight.

The pH of the developer is from about 2 to about 6, preferably 2.5 to 4.5. Any variety of non-toxic acids or buffers may be employed to maintain the acidic pH of the developer phase. Phosphoric acid is the most preferred acidifier for the developer phase.

The tint phase of the present invention has a low water content and a high organic content, but surprisingly exhibits a very low or no VOC. The amount of water in the tint phase should be less than 50 weight percent based on the total weight of the tint phase, preferably less than 40 weight percent and most preferably about 8 to about 37 weight percent based on the total weight of the tint phase.

The organic content of the tint phase is maintained at a high level by selecting a unique combination of no VOC organic solvents and organic thickeners. Examples of no VOC organic solvents are ethoxydiglycol, propylene glycol, hexylene glycol, glycerin or any combination of the foregoing. The amount of no VOC solvent employed in the present invention should be an amount sufficient to solubilize the thickeners and produce a pourable solution that mixes easily with the aqueous developer phase. Preferably, the no VOC organic solvent should comprise about 10 to about 50 weight percent of the total weight of the tint phase and most preferably about 25 to about 40 weight percent of the total weight of the tint phase.

The thickeners employed in the tint phase of the present invention should be present at a level sufficient to produce a desired viscosity and Theological profile, i.e. shampoo form or brush application. Preferably the thickeners should comprise about 5 to about 60 weight percent of the total weight of the tint phase and most preferably about 10 to about 50 weight percent of the total weight of the tint phase. Examples of the preferred thickeners are fatty acids, preferably $C_{16}$–$C_{20}$ unsaturated fatty acids such as oleic acid, linoleic acid or stearic acid, fatty alcohols, preferably $C_{10}$–$C_{20}$ fatty alcohols such as oleyl alcohols, cetyl alcohols, lauryl alcohols, ethoxylated fatty alcohols, preferably $C_{10}$–$C_{20}$ ethoxylated fatty alcohols such as laureth-4, oleth-3, oleth-5 and deceth-3, emulsifying waxes such as PEG-150 Pentaerythrityl Tetrastearate or POLAWAX which is commercially available from Croda, Inc., fatty amides, fatty amides such as cocamide MEA, cocamide DEA, lauramide DEA, and related materials such as cocamidopropyl betaine that have unsaturated $C_{10}$–$C_{20}$ fatty acid groups.

The thickener can also be any combination of the above exemplified thickeners, however, in an especially preferred embodiment, the thickeners comprise about 5 to about 20 weight percent of the total weight of the tint phase of a fatty acid thickener and about 10 to about 30 weight percent based on the total weight of the tint phase of a thickener selected from the group consisting of fatty alcohols, ethoxylated fatty alcohols, fatty amides, emulsifying waxes or any combination of the foregoing.

The dye employed in the present invention should comprise about 0 to about 10 weight percent and preferably 0.01 to about 10 weight percent of the total weight of the tint phase. If no dye is present, the alkaline agent then acts to oxidize or destroy the natural melanin pigment of the hair causing the hair to lighten. Preferably, the dye employed in the present invention is an oxidative dye precursor and comprises one or more primary intermediates together with one or more couplers. The combination of specific intermediates and/or couplers will determine the ultimate color of the treated hair.

A wide variety of intermediates and couplers may be employed in the present invention such as p-phenylenediamine, m-phenylenediamine, 4-amino-2-hydroxytoluene, 1-napthol, resorcinol, chlororesorsinol, p-aminophenol and m-aminophenol. Other intermediates and couplers are described in U.S. Pat. No. 5,376,146 and are incorporated herein by reference.

The tint phase should also comprise an alkalizer in an amount that is sufficient to maintain the pH of the combined tint phase and developer phase between 6 and 12. Any alkalizer commonly known in the industry can be used but the preferred alkalizers are ethanolamine, ammonia, aminomethylpropanol, triethanolamine, ammonium hydroxide, sodium hydroxide, potassium hydroxide, sodium carbonate, potassium phosphate, sodium carbonate, potassium carbonate, sodium silicate or mixtures of the foregoing. Generally, about 5 to about 25 weight percent and preferably 2 to 15 weight percent of the alkalizer based upon the total weight of the tint phase will be necessary to obtain and maintain the desired pH range for the hair coloring or dyeing composition.

Quaternary ammonium salts such as behentrimonium chloride, cetrimonium chloride and stearalkonium chloride and those described in U.S. Pat. No. 5,376,146, which is incorporated herein by reference, may also be incorporated into the tint phase of the present invention. The quaternary ammonium salts neutralize the anionic charge on the keratin and the alkyl groups in the ammonium salt improve the lubricity of the hair. Thus, the quaternary ammonium salts function as a hair conditioner and also as a surfactant. The concentration of the quaternary ammonium salt in the tint phase is about 0.1 to about 5.0 weight percent based upon the total weight of the tint phase.

Other conventional additives may be present in the tint phase such as fragrances, coloring agents, chelating agents, antioxidants such as sodium sulfite erythroboric acid and ascorbic acid, solubilizing agents such as sodium sulfite and mixtures of the foregoing.

The tint phase and developer phase are mixed together in a suitable vessel such as a bowl or cup just before application to the hair. The mixture will form a composition that has sufficient stay-put ability so that it will remain on the hair for the coloring period without dripping or running. The dye, intermediate and coupler, diffuse into the hair along with the oxidizing agent to react to form large molecules that remain in the hair to change the color. At the end of the coloring period, the residue of the hair coloring or dyeing composition is washed from the hair with an ordinary water rinse and shampoo while the reacted dye material remains with the hair for a number of washings.

The tint phase and the developer phase may be mixed together on the hair of the user. If the components are mixed together on the hair, it is preferred that the tint phase be added to the hair first, followed the developer phase.

The components of the present invention are packaged separately and will be mixed together by the user. The individual components may be sold separately or together in a kit. The usual ratio of developer phase to tint phase will be a weight ratio of 0.25:1 to 1:0.25 and preferably 1:1.

The invention also includes a prepackaged hair lightening or hair dyeing kit. These kits will include in a single package, one container of the developer phase and one container of the tint phase. The quantities of each phase will be sufficient for a single application and will be between 30 and 100 ml of each phase.

DESCRIPTION OF THE PREFERRED EMBODIMENTS

Tint phases in accordance with the present invention are prepared that have the compositions as described in Table 1.

EXAMPLE 1

60 ml of tint phase T1 and 60 ml of developer phase D2 are mixed together in an applicator bottle and then applied to human hair for 30 minutes to produce a dark neutral blonde color.

EXAMPLE 2

60 ml of tint phase T2 and 60 ml of developer phase D3 are mixed together in an applicator bottle and then applied to human hair for 15 minutes to produce an auburn color.

EXAMPLE 3

50 ml of tint phase T3 and 50 ml of developer phase D1 are mixed together in an applicator bottle and then applied to human hair for 5 minutes to produce an ash blonde color.

TABLE 1

| | T1 | T2 | T3 | T4 | T5 | T6 | T7 | T8 |
|---|---|---|---|---|---|---|---|---|
| water | 33.050 | 36.900 | 23.100 | 17.300 | 27.480 | 33.700 | 17.200 | 8.500 |
| ethanolamine | 5.000 | — | — | 20.000 | 3.000 | 12.000 | — | — |
| ammonia (28%) | — | — | 8.000 | — | 6.000 | — | — | — |
| aminomethylpropanol | — | 6.000 | — | — | — | — | 7.000 | — |
| ethoxydiglycol | 14.000 | 10.000 | 25.000 | — | 15.000 | 8.000 | — | — |
| propylene glycol | 14.000 | 10.000 | — | 10.000 | — | 9.000 | 20.000 | — |
| hexylene glycol | — | — | — | 10.000 | 14.000 | — | — | — |
| glycerin | — | — | 5.000 | 10.000 | — | — | 7.000 | 40.000 |
| oleic acid | 14.000 | 12.000 | 10.000 | 15.000 | — | — | — | — |
| oleyl alcohol | 8.000 | 5.000 | 10.000 | 12.000 | 7.000 | 5.000 | — | 10.000 |
| cetyl alcohol | — | 1.000 | — | — | — | 1.000 | — | — |
| lauryl alcohol | — | 5.000 | 5.000 | — | — | 5.000 | 10.000 | — |
| laureth-4 | 7.000 | 5.000 | 8.000 | — | — | — | 5.000 | — |
| cocamide DEA | 4.000 | — | — | — | 5.000 | 5.000 | — | — |
| lauramide DEA | — | 5.000 | 5.000 | 5.000 | — | — | — | — |
| triethanolamine | — | — | — | — | — | — | — | 10.000 |
| linoleic acid | — | — | — | — | 13.000 | 10.000 | 15.000 | 9.000 |
| stearic acid | — | — | — | — | — | 2.000 | 1.000 | — |
| oleth-3 | — | — | — | — | 5.000 | — | 2.000 | 10.000 |
| oleth-5 | — | — | — | — | — | — | 5.000 | 10.000 |
| deceth-3 | — | — | — | — | — | 5.000 | — | — |
| emulsifying wax | — | — | — | — | — | — | 3.000 | — |
| p-phenylenediamine | 0.300 | 1.000 | 0.400 | — | 0.200 | 1.000 | 3.500 | 1.200 |
| 4-amino-2-hydroxytoluene | — | 1.500 | — | — | — | 1.000 | — | — |
| 1-napthol | 0.050 | — | 0.100 | — | 0.050 | 0.200 | — | — |
| resorcinol | 0.200 | 0.500 | 0.100 | 0.200 | — | 0.600 | 1.500 | 0.700 |
| p-aminophenol | 0.100 | 1.000 | — | 0.300 | — | 1.200 | — | — |
| m-aminophenol | 0.200 | — | 0.200 | 0.100 | 0.070 | 0.200 | 1.000 | 0.600 |
| m-phenylenediamine | — | — | — | — | — | — | 0.200 | — |
| 4-chlororesorsinol | — | — | — | — | 0.100 | — | 1.500 | — |
| cocamidopropyl betaine | — | — | — | — | 2.000 | — | — | — |
| cetrimonium chloride | — | — | — | — | 2.000 | — | — | — |
| sodium sulfite | 0.100 | 0.100 | 0.100 | 0.100 | 0.100 | 0.100 | 0.100 | — | all amounts in Table 1 are weight percents based upon total weight of tint phase Developer phases in accordance with the present invention are prepared that have the following compositions.

| | D1 | D2 | D3 | D4 |
|---|---|---|---|---|
| water | 96.875 | 93.935 | 92.780 | 90.970 |
| hydrogen peroxide | 3.000 | 6.000 | 7.000 | 9.000 |
| disodium EDTA | 0.100 | 0.050 | 0.200 | 0.020 |
| phenacetin | 0.010 | 0.010 | — | — |
| phosphoric acid | 0.005 | 0.005 | 0.010 | 0.010 |
| sodium stannate | 0.010 | — | 0.010 | — |

EXAMPLE 4

30 ml of tint phase T4 and 60 ml of developer phase D4 are mixed together in an applicator bottle and then applied to human hair for 45 minutes to produce an extra light gold blonde color.

EXAMPLE 5

30 ml of tint phase T5 and 30 ml of developer phase D3 are mixed together in a bowl and then applied to human hair for 5 minutes to produce a cool blonde color.

EXAMPLE 6

60 ml of tint phase T6 and 60 ml of developer phase D1 are mixed together in a bowl and then applied to human hair for 10 minutes to produce a reddish brown color.

EXAMPLE 7

45 ml of tint phase T7 and 90 ml of developer phase D1 are mixed together in a bowl and then applied to human hair for 15 minutes to produce a black color.

EXAMPLE 8

30 ml of tint phase T8 and 45 ml of developer phase D1 are mixed together in an applicator bottle and then applied to human hair for 20 minutes to produce a dark brown color.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A hair dyeing composition consisting essentially of:
   (a) a developer phase consisting of:
      (i) water; and
      (ii) an oxidizing agent, wherein the developer phase has a viscosity of about 1 cps to about 5,000 cps; and
   (b) a tint phase consisting essentially of:
      (i) 0–40 weight percent water;
      (ii) 0.01–10 weight percent dye;
      (iii) 25–40 weight percent of a non volatile organic solvent that exhibits a vapor pressure of less than 0.1 mm Hg, wherein said non volatile organic solvent is selected from the group consisting of ethoxydiglycol, hexylene glycol, glycerin, and combinations thereof;
      (iv) from about 5 to about 20 weight percent based of the total weight of the tint phase of a fatty acid thickener, and from about 10 to about 30 weight percent based on the total weight of the tint phase of a thickener selected from the group consisting of fatty alcohols, emulsifying waxes, and combinations thereof, wherein the total amount thickener in the hair dyeing composition is from 10–50 weight percent;
      (v) 5–25 weight percent of an alkalizer; and
      (vi) optionally, an additive selected from the group consisting of quaternary ammonium salts, fragrances, chelating agents, antioxidants, solubilizing agents, and mixtures of the foregoing.

2. The composition as defined in claim 1 wherein the water comprises about 8 to about 37 weight percent of the total weight of the tint phase.

3. The composition as defined in claim 1 wherein the alkalizer is selected from the group consisting of ethanolamine, ammonia, aminomethylpropanol, triethanolamine, ammonium hydroxide, sodium hydroxide, potassium hydroxide, sodium carbonate, potassium phosphate, potassium carbonate, sodium silicate and mixtures of the foregoing.

4. The hair dyeing composition as defined in claim 1 wherein the composition has a viscosity of approximately 1,000 cps to approximately 100,000 cps.

5. A hair dyeing composition as defined in claim 1 where the fatty acid thickener is selected from the group consisting of $C_{16}$–$C_{20}$ unsaturated fatty acids.

6. A hair dyeing composition as defined in claim 1 where the fatty alcohol is selected from the group consisting of oleyl alcohols, cetyl alcohols, and lauryl alcohols.

7. A hair dyeing composition as defined in claim 1 where the emulsifying wax is polyethylene glycol 150-pentaerythrityl tetrastearate.

* * * * *